(12) United States Patent
Phanstiel

(10) Patent No.: US 7,728,041 B2
(45) Date of Patent: Jun. 1, 2010

(54) MOTUPORAMINE MIMIC AGENTS

(75) Inventor: Otto Phanstiel, Oviedo, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 268 days.

(21) Appl. No.: 11/371,945

(22) Filed: Mar. 14, 2006

(65) Prior Publication Data

US 2007/0213397 A1  Sep. 13, 2007

Related U.S. Application Data

(60) Provisional application No. 60/781,963, filed on Mar. 13, 2006.

(51) Int. Cl.
*A01N 33/02* (2006.01)
*A01N 33/18* (2006.01)
*A01N 33/24* (2006.01)
*A61K 31/135* (2006.01)
*A61K 31/04* (2006.01)

(52) U.S. Cl. ..................................... 514/656; 514/741
(58) Field of Classification Search ....................... None
See application file for complete search history.

(56) References Cited

OTHER PUBLICATIONS

Wang et al., Molecular Requirements for Targeting the Polyamine Transport System. J. Med. Chem., 2003, 46, 2672-2682.*
Wang et. al., Synthesis and Biological Evaluation of N1-(Anthracen-9-ylmethyl)triamines as Molecular Recognition Elements for the Polyamine Transporter, J. Med. Chem., 46 (13), 2663-2671, 2003.*
Breitbeil et al, "Modeling the Preferred Shapes of Polymaine Transpoter Ligands and Dihydromotuporamine-C Mimics: Shovel versus Hoe", J. Med. Chem. 49, pp. 2407-2416 (2006).*

* cited by examiner

*Primary Examiner*—David J Blanchard
*Assistant Examiner*—Barbara Frazier
(74) *Attorney, Agent, or Firm*—Timothy H. Van Dyke; Beusse Wolter Sanks Mora & Maire

(57) ABSTRACT

Disclosed herein are motuporamine mimic agents and methods of making and using same. Particularly exemplified are motuporamine mimic agents comprising cytotoxic activity and/or anti-metaplastic activity.

3 Claims, 5 Drawing Sheets

1: Motuporamine A

2: Motuporamine B

3 : Motuporamine C

4a: Dihydromotuporamine C; n=1, x=1, y=1
4b: n=1, x=2, y=2
4c: n=2, x=1, y=1

5 : carbazole

6a: x=1, y=1, z=1
6b: x=1, y=2, z=2
6c: x=2, y=2, z=2
6d: x=3, y=2, z=2

7a: y=1, z=1
7b: y=2, z=2

Scheme 1[a]

[a]Reagents: (a) 25% MeOH/CH$_2$Cl$_2$; (b) 50% MeOH/CH$_2$Cl$_2$, NaBH$_4$; (c) K$_2$CO$_3$, CH$_3$CN, C$_2$H$_5$Br; (d) 4N HCl/ EtOH

Scheme 2[a]

[a]Reagents: (a) 25% MeOH/CH$_2$Cl$_2$; (b) 50% MeOH/CH$_2$Cl$_2$, NaBH$_4$; (c) K$_2$CO$_3$, CH$_3$CN, C$_2$H$_5$Br; (d) 4N HCl/ EtOH

**for compounds 14b, 12b, and 12c, n=1

Scheme 3[a]

[a]Reagents: (a) MsCl / NEt$_3$ / CH$_2$Cl$_2$; (b) 3-Ethoxypropylamine or aminopropanol / CH$_3$CN; (c) EtOH / 4N HCl Scheme 4[a]

[a]Reagents : (a) Na$_2$CO$_3$/ CH$_2$Cl$_2$ ; (b) N-Acetoxysuccinimide / K$_2$CO$_3$ / CH$_2$Cl$_2$ ;(c) EtOH / 4N HCl

MOTUPORAMINE MIMIC AGENTS

CROSS-REFERENCE TO RELATED APPLICATIONS

This application is related to a U.S. Provisional Application of the same title and Applicant name filed Mar. 13, 2006, and assigned Ser. No. 60/781,963 to which priority is claimed under 35 USC §119(e).

BACKGROUND

The nonselective delivery of drugs to both targeted tumor cells and healthy cells is a major shortcoming of current chemotherapies. Enhanced cell targeting during drug delivery could diminish nonspecific toxicities by reducing uptake by healthy cells. Using existing cellular transporters for drug delivery provides opportunities for molecular recognition events to assist in the cell targeting process.

Ever since the published report of the discovery of motuporamines (see 1-3 FIG. 1), naturally occurring anti-cancer agents, found off the coast (Motupore Island) of new Guinea, the molecular structure and their bio-functions have fascinated biochemists (Williams et al., *J. Org Chem* 1998, 63:4838:4841; Williams et al., *J. Org. Chem* 2002, 67:245-248; Roskelley et al., *Cancer Res.* 2001, 61:6788-6794). Indeed, In light of the difficulty and expense of obtaining and purifying natural motuporamines, efforts have been made toward developing analogous compounds having similar or better characteristics that may be synthetically manufactured. Dihydromotuporamine C, (see 4a, FIG. 1) comprises a fifteen-membered ring, which is difficult to synthesize unless one uses expensive metal catalysts like Grubb's catalyst.

DETAILED DESCRIPTION

Figure 1:
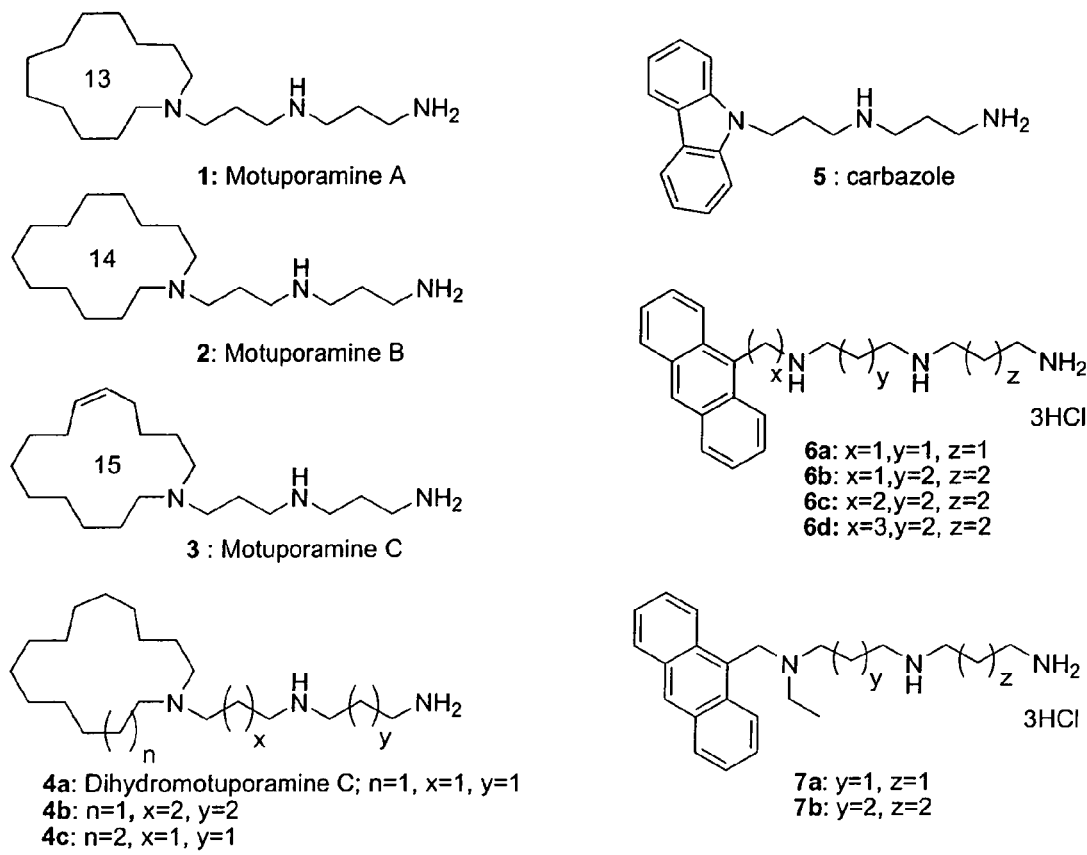
FIG. 1 shows structures of motuporamine mimic agents.

The invention pertains to motuporamine mimic agents (MMA) and synthesis thereof that are cytotoxic to cancer cells and optionally also inhibit their spread to other tissues (i.e., their metastatic behavior). The invention is based in part on the inventors' realization that less costly and easily synthesized motuporamine mimic agents are needed and desired. According to one aspect, the subject invention pertains to MMAs that have similar biological potency as compound 4a (see FIG. 1), yet are much easier to synthesize and provide a cost-efficient entry into this novel drug class. It is difficult chemically to synthesize 4a. There are several reports (Goldring, W. P. D.; Weiler, L. Cytotoxic Alkaloids Motuporamines A-C: Synthesis and Structural Verification, *Org. Letters* 1999, 1(9); 1471-1473; Furstner, A.; Rumbo, A. Ring-Closing Alkyne Metathesis. Stereoselective Synthesis of the Cytotoxic Marine Alkaloid Motuporamine C, *J. Org. Chem.* 2000, 65(8); 2608-2611), which synthesize 4a through lengthy synthesis steps involving expensive metal catalysts.

Figure 2:
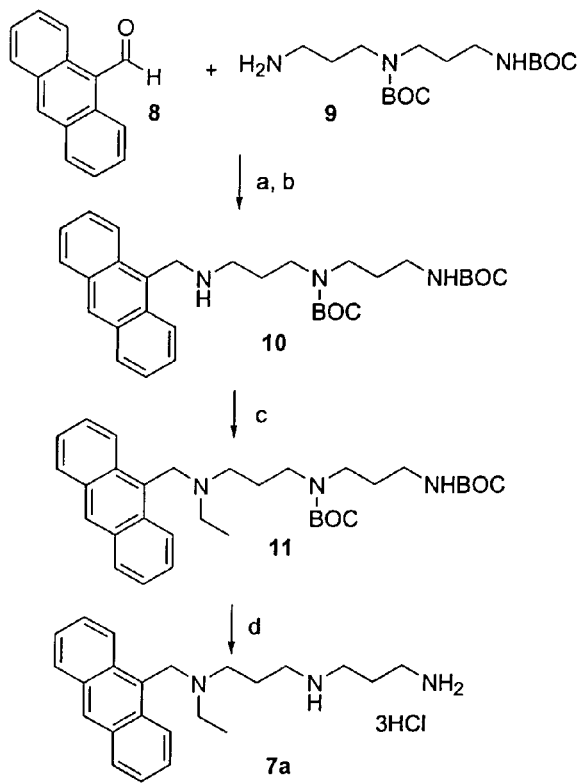
FIG. 2 shows a scheme for synthesizing motuporamine mimic agents.
Figure 3:
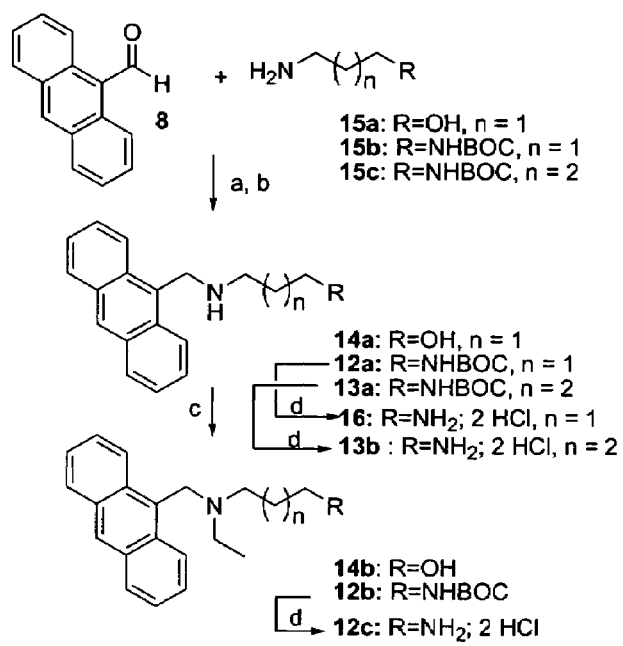
FIG. 3. shows a scheme for synthesizing motuporamine mimic agents.
Figure 4:
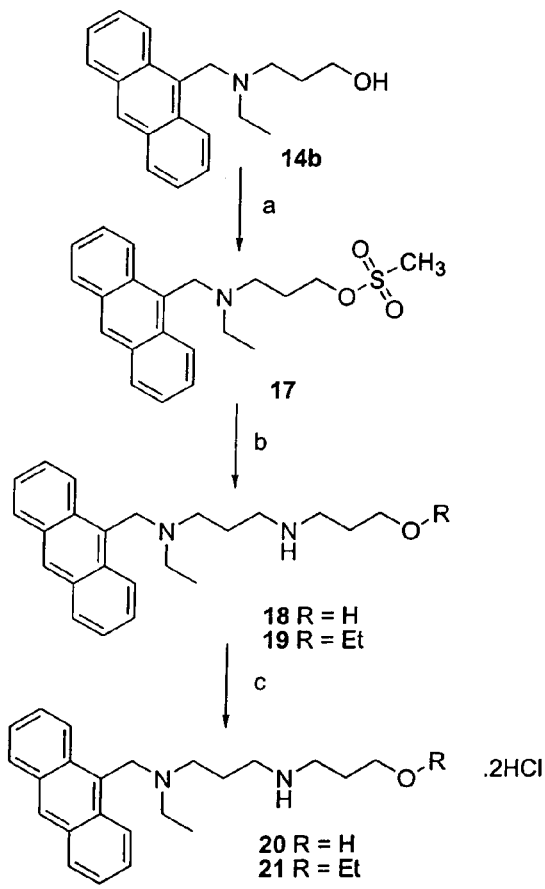
FIG. 4 shows a scheme for synthesizing motuporamine mimic agents.
Figure 5:
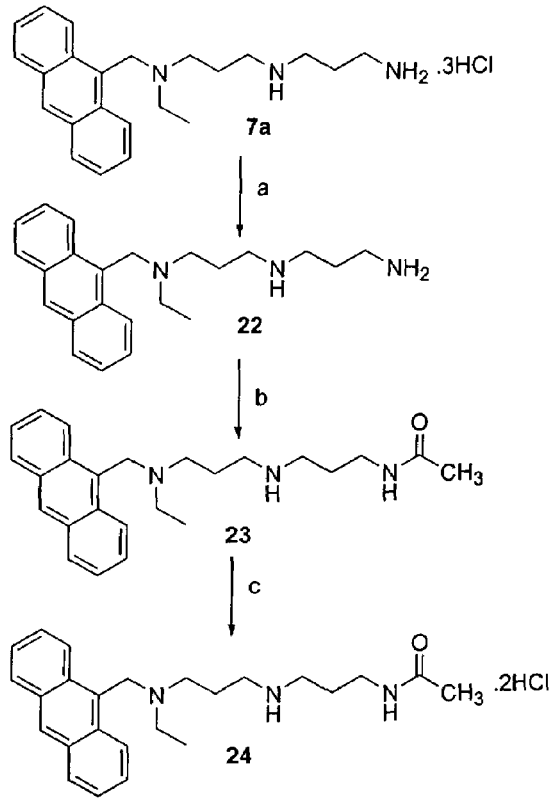
FIG. 5 shows a scheme for synthesizing motuporamine mimic agents.

Certain MMA embodiments; of the subject invention such as, but not limited to, compounds 7a, 7b, 12 and 14, are more readily synthesized via synthesis schemes of the subject invention, including schemes 1 and 2 shown in FIGS. 2 and 3, respectively. Not being held to any particular theory, it is the inventors belief that the large anthracene ring system can substitute (and behave biologically) like the 15-membered ring of 4a. Alternate embodiments of the subject invention include, but are not limited to, 14b 17, 18, 19, 20, 21, as synthesized according to scheme 3 (FIG. 4) and compounds 22, 23, and 24 as synthesized according to scheme 4 (FIG. 5. Furthermore, other embodiments of the subject invention pertain to the synthesis processes disclosed in FIGS. 2-5, or portions thereof.

Certain MMA embodiments of the subject invention, such as, but not limited to 7a, 7b, 12 and 14 not only are good anticancer agents via their cytotoxic properties, but they also serve as anti-metastatic agents which block the spread of cancer cells (a common problem encountered with cancer patients). A non-toxic anti-metastatic agent would also be of use to cancer patients because it could be taken as a cancer preventative and/or as an anti-metastatic agent along with a different chemotherapeutic regimen. Accordingly, cytotoxic agents like 7a are helpful toward halting the spread of cancer as well as killing cancer cells.

In a specific embodiment, MMAs according to the subject invention comprise the following structure:

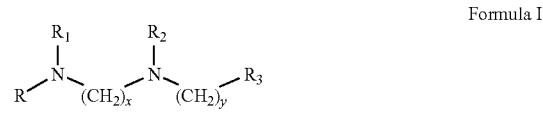

Formula I where R is alkylaryl (wherein the aryl ring is either a benzene, naphthalene, anthracene or pyrene ring system and the alkyl chain length is either methylene, ethylene, propylene, butylene, pentylene or hexylene), alkyl, cycloalkyl;

$R_1$ is either hydrogen or linear alkyl (methyl, ethyl, propyl, butyl, pentyl or hexyl) or branched alkyl (isopropyl, isobutyl, sec-butyl or t-butyl), or alkylaryl (wherein the aryl ring is either a benzene, naphthalene, anthracene or pyrene ring system and the alkyl chain length is either methylene, ethylene, propylene, butylene, pentylene or hexylene), $R_2$ is either hydrogen, alkyl, alkylaryl or aryl or equivalent to the —(CH2)y$R_3$ $R_3$ is either hydrogen (H), or hydroxy (—OH), or alkoxy (—O-alkyl) or alkylamido (—NHCOalkyl), amino (—NH2) or amino alkyl (—NH-alkyl), or N-alkyl, N-alkylamido, or Nalkylaryl,N-alkyl amino, x=1-16 and y=1-16 and pharmaceutically relevant inorganic salts thereof. MMA agents include pharmaceutically acceptable inorganic salts of the MMA agents (e.g., trihydrochloride salt, 3 HCl salt of skeleton 1). Other embodiments of the subject invention pertain to methods of synthesizing MMA agents.

Certain preferred MMA embodiments include the following:

1: R=anthracen-9-ylmethyl, $R_1$=ethyl, $R_2$=H, $R_3$=NH2, x=3, and y=3

2: R=anthracen-9-ylmethyl, $R_1$=ethyl, $R_2$=H, $R_3$=NH2, x=4, and y=4

3: R=anthracen-9-ylmethyl, $R_1$=ethyl, $R_2$=H, $R_3$=OH, x=3, and y=3

4: R=anthracen-9-ylmethyl, $R_1$=ethyl, $R_2$=H, $R_3$=NHCOCH3, x=3, and y=3

5: R=anthracen-9-ylmethyl, $R_1$=ethyl, $R_2$=H, $R_3$=OCH2CH3, x=3, and y=3

6: R=anthracen-9-ylmethyl, $R_1$=H, $R_2$=H, $R_3$=NH2, x=3, and y=3

7: R=anthracen-9-ylmethyl, $R_1$=H, $R_2$=BOC, $R_3$=NHBOC, x=3, and y=3

8: R=anthracen-9-ylmethyl, $R_1$=ethyl, $R_2$=BOC, $R_3$=NHBOC, x=3, and y=3

9: R=anthracen-9-ylmethyl, $R_1$=H, $R_2$=BOC, $R_3$=NHBOC, x=4, and y=4

10: R=anthracen-9-ylmethyl, $R_1$=ethyl, $R_2$=BOC, $R_3$=NHBOC, x=4, and y=4

11: R=anthracen-9-ylmethyl, $R_1$=ethyl, $R_2$=H, $R_3$=NHCOR$_4$, where $R_4$ is linear or branched alkyl, aryl or alkylaryl, x=3, and y=3

In an alternative embodiment, MMAs according to the subject invention comprise the following structure:

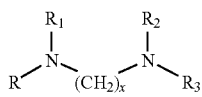

Formula II

13: R=anthracen-9-ylmethyl, $R_1$=ethyl, $R_2$=H, $R_3$=H, x=3
14: R=anthracen-9-ylmethyl, $R_1$=ethyl, $R_2$=H, $R_3$=BOC (t-butylcarbonyloxy), x=3
15: R=anthracen-9-ylmethyl, $R_1$=H, $R_2$=H, $R_3$=H, x=3
16: R=anthracen-9-ylmethyl, $R_1$=H, $R_2$=H, $R_3$=BOC (t-butylcarbonyloxy), x=3

In an alternative embodiment, MMAs according to the subject invention comprise the following structure:

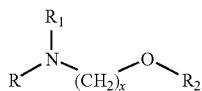

Formula III

17: R=anthracen-9-ylmethyl, $R_1$=ethyl, $R_2$=H, x=3
18: R=anthracen-9-ylmethyl, $R_1$=H, $R_2$=H, x=3

The following structures are those referred to in the formulas above:

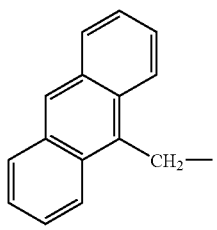

Formula IV anthracen-9-ylmethyl

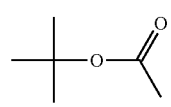

Formula V tert-butylcarbonyloxy (BOC group)

Pharmaceutical Compositions

The invention also pertains to pharmaceutical compositions which can be administered to a patient to achieve a therapeutic effect, e.g., cytotoxicity of cancer cells in a subject and/or metastatic behavior. Pharmaceutical compositions of the invention can comprise, for example, a Motuporamine Mimic Agent (MMA). The compositions can be administered alone or in combination with at least one other agent, such as stabilizing compound, which can be administered in any sterile, biocompatible pharmaceutical carrier, including, but not limited to, saline, buffered saline, dextrose, and water. The compositions can be administered to a patient alone, or in combination with other agents, drugs or hormones.

In addition to the active ingredients, these pharmaceutical compositions can contain suitable pharmaceutically acceptable carriers comprising excipients and auxiliaries which facilitate processing of the active compounds into preparations which can be used pharmaceutically. Pharmaceutical compositions of the invention can be administered by any number of routes including, but not limited to, oral, intravenous, intramuscular, intra-arterial, intramedullary, intrathecal, intraventricular, transdermal, subcutaneous, intraperitoneal, intranasal, parenteral, topical, sublingual, or rectal means. Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethylcellulose, or sodium carboxymethylcellulose; gums including arabic and tragacanth; and proteins such as gelatin and collagen. If desired, disintegrating or solubilizing agents can be added, such as the cross-linked polyvinyl pyrrolidone, agar, alginic acid, or a salt thereof, such as sodium alginate.

Dragee cores can be used in conjunction with suitable coatings, such as concentrated sugar solutions, which also can contain gum arabic, talc, polyvinylpyrrolidone, carbopol gel, polyethylene glycol, and/or titanium dioxide, lacquer solutions, and suitable organic solvents or solvent mixtures. Dyestuffs or pigments can be added to the tablets or dragee coatings for product identification or to characterize the quantity of active compound, i.e., dosage.

Pharmaceutical preparations which can be used orally include push fit capsules made of gelatin, as well as soft, sealed capsules made of gelatin and a coating, such as glycerol or sorbitol. Push fit capsules can contain active ingredients mixed with a filler or binders, such as lactose or starches, lubricants, such as talc or magnesium stearate, and, optionally, stabilizers. In soft capsules, the active compounds can be dissolved or suspended in suitable liquids, such as fatty oils, liquid, or liquid polyethylene glycol with or without stabilizers.

Pharmaceutical formulations suitable for parenteral administration can be formulated in aqueous solutions, preferably in physiologically compatible buffers such as Hanks' solution, Ringer's solution, or physiologically buffered saline. Aqueous injection suspensions can contain substances which increase the viscosity of the suspension, such as sodium carboxymethyl cellulose, sorbitol, or dextran. Additionally, suspensions of the active compounds can be prepared as appropriate oily injection suspensions. Suitable lipophilic solvents or vehicles include fatty oils such as sesame oil, or synthetic fatty acid esters, such as ethyl oleate or triglycerides, or liposomes. Non-lipid polycationic amino polymers also can be used for delivery. Optionally, the suspension also can contain suitable stabilizers or agents which increase the solubility of the compounds to allow for the preparation of highly concentrated solutions. For topical or nasal administration, penetrants appropriate to the particular barrier to be permeated are used in the formulation. Such penetrants are generally known in the art.

The pharmaceutical compositions of the present invention can be manufactured in a manner that is known in the art, e.g., by means of conventional mixing, dissolving, granulating, dragee making, levigating, emulsifying, encapsulating, entrapping, or lyophilizing processes. The pharmaceutical composition can be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation can be a lyophilized powder which can contain any or all of the following: 150 mM histidine, 0.1% 2% sucrose, and 27% mannitol, at a pH range of 4.5 to 5.5, that is combined with buffer prior to use.

In one embodiment, the reagent is delivered using a liposome. Preferably, the liposome is stable in the animal into which it has been administered for at least about 30 minutes, more preferably for at least about 1 hour, and even more preferably for at least about 24 hours. A liposome comprises a lipid composition that is capable of targeting a reagent, particularly a polynucleotide, to a particular site in an animal, such as a human. Preferably, the lipid composition of the liposome is capable of targeting to a specific organ of an animal, such as the lung, liver, spleen, heart brain, lymph nodes, and skin.

A liposome useful in the present invention comprises a lipid composition that is capable of fusing with the plasma membrane of the targeted cell to deliver its contents to the cell. Preferably, the transfection efficiency of a liposome is about 0.5 µg of DNA per 16 nmole of liposome delivered to about 106 cells, more preferably about 1.0 µg of DNA per 16 nmole of liposome delivered to about $10^6$ cells, and even more preferably about 2.0 µg of DNA per 16 nmol of liposome delivered to about $10^6$ cells. Preferably, a liposome is between about 100 and 500 nm, more preferably between about 150 and 450 nm, and even more preferably between about 200 and 400 nm in diameter.

Suitable liposomes for use in the present invention include those liposomes standardly used in, for example, gene delivery methods known to those of skill in the art. More preferred liposomes include liposomes having a polycationic lipid composition and/or liposomes having a cholesterol backbone conjugated to polyethylene glycol. Optionally, a liposome comprises a compound capable of targeting the liposome to a particular cell type, such as a cell-specific ligand exposed on the outer surface of the liposome.

Determination of a Therapeutically Effective Dose

The determination of a therapeutically effective dose is well within the capability of those skilled in the art. A therapeutically effective dose refers to that amount of active ingredient which causes cytotoxicity of cancer cells in a subject and/or metastatic behavior which occurs in the absence of the therapeutically effective dose.

For any compound, the therapeutically effective dose can be estimated initially either in cell culture assays or in animal models, usually mice, rabbits, dogs, or pigs. The animal model also can be used to determine the appropriate concentration range and route of administration. Such information can then be used to determine useful doses and routes for administration in humans.

Therapeutic efficacy and toxicity, e.g., $ED_{50}$ (the dose therapeutically effective in 50% of the population) and $LD_{50}$ (the dose lethal to 50% of the population), can be determined by standard pharmaceutical procedures in cell cultures or experimental animals. The dose ratio of toxic to therapeutic effects is the therapeutic index, and it can be expressed as the ratio, $LD_{50}/ED_{50}$.

Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the $ED_{50}$ with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active ingredient or to maintain the desired effect. Factors which can be taken into account include the severity of the disease state, general health of the subject, age, weight, and gender of the subject, diet, time and frequency of container and labeled for treatment of an indicated condition. Such labeling would include amount, frequency, and method of administration.

Normal dosage amounts can vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors.

In any of the embodiments described above, any of the pharmaceutical compositions of the invention can be administered in combination with other appropriate therapeutic agents. Selection of the appropriate agents for use in combination therapy can be made by one of ordinary skill in the art, according to conventional pharmaceutical principles. The combination of therapeutic agents can act synergistically to effect the treatment or prevention of the various disorders described above. Using this approach, one may be able to achieve therapeutic efficacy with lower dosages of each agent, thus reducing the potential for adverse side effects.

Any of the therapeutic methods described above can be applied to any subject in need of such therapy, including, for example, mammals such as dogs, cats, cows, horses, rabbits, monkeys, and most preferably, humans.

EXAMPLE 1

Synethesis of N-(3-Amino-propyl)-N'-anthracen-9-ylmethyl-N'-ethyl-propane-1,3-diamine, Hydrochloride salt (7a)

Materials. Materials for Examples 1-16. Silica gel (32-63 µm) and chemical reagents were purchased from commercial sources and used without further purification. All solvents were distilled prior to use. All other reactions were carried out under an $N_2$ atmosphere. $^1H$ and $^{13}C$ spectra were recorded at 300 or 75 MHz, respectively. TLC solvent systems are listed as volume percents and NH$_4$OH refers to concentrated aqueous NH$_4$OH.

A solution of BOC-protected 11 (700 mg, 1.28 mmole) was dissolved in absolute ethanol (13 mL) and stirred at 0° C. for 10 minutes. A 4N HCl solution (22 mL) was added to the reaction mixture dropwise and stirred at 0° C. for 20 minutes and then at room temperature overnight. The solution was concentrated in vacuo to give 7a as a yellow solid in 90% yield. $^1$H NMR (D$_2$O) δ 8.23 (s, 1H), 7.91 (m, 4H), 7.70 (m, 2H), 7.59 (m, 2H), 4.70 (s, 2H), 3.34 (m, 2H), 3.11 (m, 4H), 3.00 (t, 2H), 2.84 (t, 2H), 2.05 (q, 2H), 1.96 (m, 2H), 1.41 (m, 3H); $^{13}$C NMR (D$_2$O): δ 133.7, 133.1 (3C), 132.3 (2C), 130.7 (2C), 128.1 (2C), 125.0 (2C), 121.1 (2C), 52.1, 51.8, 47.3, 47.2, 39.3 (2C), 26.5, 23.5, 11.32. HRMS (FAB) calcd for C$_{23}$H$_{31}$N$_3$.3HCl (M+H−3HCl)$^+$ 350.2591, Found 350.2588.

EXAMPLE 2

Synethesis of N-(4-Amino-butyl)-N'-anthracen-9-ylmethyl-N'-ethyl-butane-1,4-diamine Hydrochloride salt (7b)

A solution of the respective Boc-protected precursor (similar to molecule 11 but having a 4,4-triamine sequence; 140 mg, 0.26 mmole) was dissolved in absolute ethanol (2.28 mL) and stirred at 0° C. for 10 minutes. A 4N HCl solution (3.64 mL) was added to the reaction mixture dropwise and stirred at 0° C. for 20 minutes and then at room temperature overnight. The solution was concentrated in vacuo to give 7b as a yellow solid in 93% yield; $^1$H NMR (D$_2$O) δ 8.76 (s, 1H), 8.23 (m, 4H), 7.78 (m, 2H), 7.68 (m, 2H), 5.33 (s, 2H), 3.43 (m, 2H), 3.19 (m, 2H), 3.04 (t, 2H), 3.00 (t, 2H), 2.83 (t, 2H), 1.74 (m, 6H), 1.47 (m, 5H); $^{13}$C NMR (CD$_3$OD): δ 133.0, 132.9, 132.6, 130.9, 129.4, 126.7, 124.3, 121.4, 53.4, 51.0, 40.1, 25.8, 24.7, 24.5, 22.3, 9.7. HRMS (FAB) calcd for C$_{25}$H$_{35}$N$_3$ (M−Cl)$^+$: 377.2831, Found 377.2831.

EXAMPLE 3

Synethesis of {3-[(Anthracen-9-ylmethyl)-amino]-propyl}-(3-tert-butoxycarbonylamino-propyl)-carbamic acid tert-butyl ester (10)

To a stirred solution of amine 9 (1 g, 3.02 mmol) in 25% MeOH/CH$_2$Cl$_2$ (20 mL), was added a solution of 9-anthraldehyde 8 (0.519 g, 2.52 mmol) in 25% MeOH/CH$_2$Cl$_2$ (15 mL) under N$_2$. The mixture was stirred at room temperature overnight until the imine formation was complete (monitored by NMR). The solvent was removed in vacuo, the solid residue dissolved in 50% MeOH/CH$_2$Cl$_2$ (40 mL) and the solution cooled to 0° C. NaBH$_4$ (7.55 mmol) was added in small portions to the solution and the mixture was stirred at rt overnight. The solvent was removed in vacuo, the solid residue dissolved in CH$_2$Cl$_2$ (40 mL) and washed with Na$_2$CO$_3$ solution (10% aq. 3×30 mL). The CH$_2$Cl$_2$ layer was dried over anhydrous Na$_2$SO$_4$, filtered and removed in vacuo to give an oily residue. The oil was purified by flash column chromatography (5% MeOH/CHCl$_3$) to yield the product 10 as a pale yellow thick oil (0.38 g, 75%), R$_f$=0.3 (5% MeOH/CHCl$_3$); $^1$H NMR (CDCl$_3$) δ 8.39 (s, 1H), 8.34 (d, 2H), 7.99 (d, 2H), 7.53 (m, 2H), 7.46 (m, 2H), 4.70 (s, 2H), 3.18-3.24 (m, 4H), 3.06 (br t, 2H), 2.85 (br t, 2H), 1.77 (br q, 2H), 1.60 (br q, 2H), 1.44 (m, 18H); $^{13}$C NMR (CDCl$_3$) δ 156.1 (2C), 131.6, 130.3 (2C), 129.2 (2C), 127.2 (2C), 126.1 (2C), 125.0 (3C), 124.2 (2C), 79.7 (2C), 53.7, 48.0, 46.0, 45.3, 44.0, 37.6, 29.6, 28.7 (6C), 27.5. HRMS (FAB) m/z calcd. for C$_{31}$H$_{43}$N$_3$O$_4$ (M+H)$^+$ 522.3326, found 522.3304.

EXAMPLE 4

Synethesis of [3-(Anthracen-9-ylmethyl-ethyl-amino)-propyl]-(3-tert-butoxycarbonylamino-propyl)-carbamic acid tert-butyl ester (11)

Ethylbromide (EtBr, 508 mg, 4.66 mmol) was dissolved in anhydrous acetonitrile and added to a stirring mixture of compound 10 (805 mg, 1.55 mmol) and anhydrous K$_2$CO$_3$ (644 mg, 4.66 mmol). The mixture was then stirred overnight at 75° C. under a N$_2$ atmosphere. After the confirmation of the disappearance of the 10 by TLC, the solution was concentrated under reduced pressure. The residue was dissolved in CH$_2$Cl$_2$ (20 mL) and washed three times with aqueous sodium carbonate. The organic layer was separated, dried with anhydrous Na$_2$SO$_4$, filtered and concentrated under vacuum. Flash column chromatography of the residue gave 11 as a light yellow oil. Yield 80%; R$_f$=0.35 (3% MeOH/CHCl$_3$); $^1$H NMR (CDCl$_3$) δ 8.43 (d, 2H), 8.25 (s, 1H), 7.86 (d, 2H), 7.43 (m, 2H), 7.37 (m, 2H), 4.34 (s, 2H), 2.78-2.92 (m, 4H), 2.64 (m, 4H), 2.36 (m, 2H), 1.21-1.48 (m, 23H), 1.16 (m, 2H); $^{13}$C NMR (CDCl$_3$) δ 155.7, 131.1 (3C), 131.0, 128.7 (2C), 127.0 (2C), 125.2 (2C), 124.8 (2C), 124.5 (2C), 78.9, 78.4, 53.4, 50.6, 50.0, 47.9, 45.3, 43.5, 37.1, 28.3 (6C), 26.5, 11.7. HRMS (FAB) m/z calcd. for C$_{33}$H$_{47}$N$_3$O$_4$ (M+H)$^+$ 550.3639, found 550.3619.

EXAMPLE 5

Synthesis of Methanesulfonic acid 3-(anthracen-9-ylmethyl-ethyl-amino)-propyl ester (17)

To a solution of the alcohol 14b (216 mg, 0.74 mmol) and triethylamine (0.31 mL, 2.21 mmol) in CH$_2$Cl$_2$ (40 mL) at 0° C., methanesulfonyl chloride (253 mg, 2.21 mmol) was added dropwise over 30 minutes under a N$_2$ atmosphere. The reaction was stirred at 0° C. for 1 hour and slowly warmed to room temperature and stirred overnight under N$_2$. The reaction was then cooled to 0° C. and a 4M NaOH solution (20 mL) was added slowly with vigorous stirring. The organic phase was separated and washed with water (2×40 mL). The organic phase was separated and dried over anhydrous Na$_2$SO$_4$, filtered and concentrated to give the product 17 as a clear oil (94%) that was used in the next step without further purification. 17: R$_f$=0.54 (1% MeOH/CH$_2$Cl$_2$); $^1$H NMR (CDCl$_3$) δ 8.47 (d, 2H), 8.36 (s, 1H), 7.98 (d, 2H), 7.52 (m, 2H), 7.47 (m, 2H), 4.43 (s, 2H, CH$_2$), 3.82 (t, 2H, OCH$_2$), 3.11 (s, 3H, CH$_3$), 2.70 (q, 2H, NCH$_2$), 2.51 (t, 2H, NCH$_2$), 1.66 (q, 2H, CH$_2$), 1.20 (t, 3H, CH$_3$).

EXAMPLE 6

Synthesis 3-[3-(Anthracen-9-ylmethyl-ethyl-amino)-propylamino]-propan-1-ol (18)

The mesylate 17 (384 mg, 1.04 mmol) and 3-amino-propanol (392 mg, 5.25 mmol) were dissolved in acetonitrile (20 mL). The mixture was then stirred at 75° C. under a N$_2$ atmosphere overnight. After the confirmation of the disappearance of the mesylate by TLC, the solution was concentrated under reduced pressure. The residue was dissolved in CH$_2$Cl$_2$ (20 mL) and washed three times with aqueous sodium carbonate. The organic layer was separated, dried with anhydrous Na$_2$SO$_4$, filtered and concentrated under vacuum. Flash column chromatography of the residue gave 18 as a light yellow oil. Yield 65%; R$_f$=0.35 (1:6:83 NH$_4$OH:

MeOH:CH$_2$Cl$_2$); $^1$H NMR (CDCl$_3$) δ 8.32 (d, 2H), 8.23 (s, 1H), 7.83 (d, 2H), 7.37 (m, 2H), 7.30 (m, 2H), 4.28 (s, 2H), 3.48 (t, 2H), 2.56 (q, 2H), 2.30 (t, 2H), 2.12 (t, 2H), 2.06 (t, 2H), 1.36 (q, 2H), 1.21 (q, 2H), 1.09 (t, 3H); $^{13}$C NMR (CDCl$_3$) δ 131.3, 131.2, 130.5, 129.3, 129.0, 127.3, 125.5, 125.3, 124.8, 124.8, 63.8, 50.8, 50.5, 49.5, 48.3, 47.7, 30.5, 26.6, 11.7. HRMS (FAB) m/z calcd. for C$_{23}$H$_{30}$N$_2$O (M+H)$^+$ 351.2431; found 351.2430.

EXAMPLE 6

Synethesis of N-Anthracen-9-ylmethyl-N'-(3-ethoxy-propyl)-N-ethyl-propane-1,3-diamine (19)

The mesylate 17 (584 mg, 1.57 mmol) and 3-ethoxypropylamine (649 mg, 6.30 mmol) were dissolved in acetonitrile (30 mL). The mixture was then stirred at 75° C. under a N$_2$ atmosphere overnight. After the confirmation of the disappearance of the mesylate by TLC, the solution was concentrated under reduced pressure. The residue was dissolved in CH$_2$Cl$_2$ (25 mL) and washed three times with aqueous sodium carbonate. The organic layer was separated, dried with anhydrous Na$_2$SO$_4$, filtered and concentrated under vacuum. Flash column chromatography of the residue gave 19 as a light yellow oil. Yield 60%; R$_f$=0.35 (0.5:4:85.5 NH$_4$OH:MeOH:CH$_2$Cl$_2$); $^1$H NMR (CDCl$_3$) δ 8.43 (d, 2H), 8.29 (s, 1H), 7.89 (d, 2H), 7.40 (m, 4H), 4.38 (s, 2H), 3.35 (q, 2H), 3.25 (t, 2H), 2.62 (q, 2H), 2.44 (t, 2H), 2.27 (t, 2H), 2.23 (t, 2H), 1.54 (q, 2H), 1.41 (q, 2H), 1.14 (m, 6H); $^{13}$C NMR (CDCl$_3$) δ 131.3, 131.2, 130.6, 128.9, 127.2, 125.4, 125.0, 124.7, 69.1, 66.0, 50.7, 50.6, 48.2, 47.5, 47.2, 30.1, 27.1, 15.4, 11.9.

EXAMPLE 7

Synethesis of N-Anthracen-9-ylmethyl-N'-(3-ethoxy-propyl)-N-ethyl-propane-1,3-diamine, Hydrochloride salt (20)

A solution of compound 18 (200 mg, 0.57 mmole) was dissolved in absolute ethanol (13 mL) and stirred at 0° C. for 10 minutes. A 4N HCl solution (22 mL) was added to the reaction mixture dropwise and stirred at 0° C. for 20 minutes and then at room temperature overnight. The solution was concentrated in vacuo to give 20 as a yellow solid in 95% yield. $^1$H NMR (D$_2$O) δ 8.50 (s, 1H), 8.06 (m, 4H), 7.73 (m, 2H), 7.62 (m, 2H), 4.98 (s, 2H), 3.64 (t, 2H), 3.39 (q, 2H), 3.13 (t, 2H), 2.90 (t, 2H), 2.76 (t, 2H), 1.79 (q, 2H), 1.44 (m, 5H); $^{13}$C NMR (D$_2$O): δ 133.8, 133.4, 132.4, 130.8, 128.3, 125.1, 121.8, 61.4, 52.4, 52.1, 52.0, 48.0, 47.0, 30.5, 23.4, 11.3. HRMS (FAB) calcd for C$_{23}$H$_3$ON$_2$O.2HCl (M+H−2HCl)$^+$ 351.2431, Found 351.2428.

EXAMPLE 8

Synthesis of N-Anthracen-9-ylmethyl-N'-(3-ethoxy-propyl)-N-ethyl-propane-1,3-diamine, Hydrochloride salt (21)

A solution of compound 19 (169 mg, 0.45 mmole) was dissolved in absolute ethanol (13 mL) and stirred at 0° C. for 10 minutes. A 4N HCl solution (22 mL) was added to the reaction mixture dropwise and stirred at 0° C. for 20 minutes and then at room temperature overnight. The solution was concentrated in vacuo to give 21 as a yellow solid in 95% yield. $^1$H NMR (D$_2$O) δ 8.58 (s, 1H), 8.10 (m, 4H), 7.73 (m, 2H), 7.62 (m, 2H), 5.12 (s, 2H), 3.52 (m, 4H), 3.43 (q, 2H), 3.15 (t, 2H), 2.84 (t, 2H), 2.73 (t, 2H), 1.79 (m, 4H), 1.47 (t, 3H), 1.15 (t, 3H); $^{13}$C NMR (D$_2$O): δ 133.9, 133.5, 132.5, 130.9, 128.4, 125.2, 122.1, 69.9, 69.3, 52.7, 52.4, 52.2, 48.1, 47.0, 28.2, 23.5, 17.0, 11.4. HRMS (FAB) calcd for C$_{25}$H$_{34}$N$_2$O.2HCl (M+H−2HCl)$^+$ 379.2749, Found 379.2749.

EXAMPLE 9

Synthesis of N-{3-[3-(Anthracen-9-ylmethyl-ethyl-amino)-propylamino]-propyl}-acetamide (23)

A saturated sodium carbonate solution (20 mL) was added to a vigorously stirred solution of 7a (250 mg, 0.55 mmol) in CH$_2$Cl$_2$ (20 mL). The organic layer was separated and was washed twice with saturated sodium carbonate. The combined organic layers were dried with anhydrous Na$_2$SO$_4$, filtered and concentrated to give the free amine 22 as a pale yellow oil in 99% yield. 22: $^1$H NMR (CDCl$_3$) δ 8.48 (d, 2H), 8.38 (s, 1H), 7.97 (d, 2H), 7.47 (m, 4H), 4.47 (s, 2H), 2.70 (q, 2H), 2.51 (m, 4H), 2.29 (t, 2H), 2.17 (t, 2H), 1.56 (q, 2H), 1.24 (m, 5H); $^{13}$C NMR (CDCl$_3$): 6 131.5, 131.4, 130.9, 129.1, 127.4, 125.6, 125.5, 125.2, 124.9, 50.8, 50.7, 48.3, 47.8, 40.7, 33.7, 27.0, 12.0.

A mixture of compound 22 (190 mg, 0.54 mmol) and anhydrous K$_2$CO$_3$ (113 mg, 0.82 mmol) in anhydrous CH$_2$Cl$_2$ was stirred at 0° C. for 10 minutes. N-Acetoxysuccinimide (NHS ester, 60 mg, 0.38 mmol) was dissolved in dry CH$_2$Cl$_2$ and was added slowly to the above stirred solution at 0° C. under N$_2$ atmosphere. The mixture was then stirred for 30 minutes at 0° C. and then slowly allowed to come at room temperature and stirred for 8 hrs. After the confirmation of the disappearance of the ester by TLC in CH$_2$Cl$_2$/hexane (7:3), the solution was filtered and concentrated under reduced pressure. The residue was dissolved in CH$_2$Cl$_2$ (20 mL) and washed three times with aqueous sodium carbonate. The organic layer was separated, dried with anhydrous Na$_2$SO$_4$, filtered and concentrated under vacuum. Flash column chromatography of the residue gave 23 as a light yellow oil. Yield 67%; R$_f$=0.30 (7% MeOH: 1% NH4OH: 82% CH$_2$Cl$_2$); $^1$H NMR (CDCl$_3$) δ 8.43 (d, 2H), 8.35 (s, 1H), 7.95 (d, 2H), 7.23 (m, 4H), 6.84 (br t, 1H), 4.43 (s, 2H), 3.05 (q, 2H), 2.71 (q, 2H), 2.43 (t, 2H), 2.20 (t, 2H), 2.09 (t, 2H), 2.78 (s, 3H), 2.48 (q, 2H), 1.21 (m, 5H); $^{13}$C NMR (CDCl$_3$) δ 170.0, 131.4, 131.3, 130.6, 129.1, 127.5, 125.7, 124.9, 124.9, 50.6, 48.1, 48.0, 48.0, 39.0, 28.2, 26.6, 23.4, 11.8. HRMS (FAB) m/z calcd. for C$_{25}$H$_{33}$N$_3$O (M+H)$^+$ 392.2701, found 392.2709.

EXAMPLE 10

Synthesis of N-{3-[3-(Anthracen-9-ylmethyl-ethyl-amino)-propylamino]-propyl}-acetamide, Hydrochloride salt (24)

A solution of compound 23 (100 mg, 0.26 mmole) was dissolved in absolute ethanol (13 mL) and stirred at 0° C. for 10 minutes. A 4N HCl solution (22 mL) was added to the reaction mixture dropwise and stirred at 0° C. for 20 minutes and then at room temperature overnight. The solution was concentrated in vacuo to give 24 as a yellow solid in 96% yield. $^1$H NMR (D$_2$O) δ 8.59 (s, 1H), 8.10 (m, 4H), 7.70 (m, 2H), 7.61 (m, 2H), 5.13 (s, 2H), 3.41 (br m, 2H), 3.12 (br m, 4H), 2.79 (br m, 4H), 1.98 (s, 3H), 1.71 (q, 2H), 1.43 (m, 5H); $^{13}$C NMR (D$_2$O): δ 174.5, 131.3, 130.8, 129.8, 128.2, 125.7, 122.5, 119.1, 50.0, 49.7, 49.4, 44.9, 44.1, 36.0, 25.5, 21.9, 20.8, 8.7. HRMS (FAB) calcd for C$_{25}$H$_{33}$N$_3$O.2HCl (M+H−2HCl)$^+$ 392.2701, Found 392.2702.

EXAMPLE 11

Synthesis of {3-[(Anthracen-9-ylmethyl)-amino]-propyl}-carbamic acid tert-butyl ester (12a)

To a stirred solution of mono-BOC protected 1,3-diamine 15b (1 g, 5.75 mmol) in 25% MeOH/CH$_2$Cl$_2$ (20 mL), was added a solution of 9-anthraldehyde 8 (0.99 g, 4.8 mmol) in 25% MeOH/CH$_2$Cl$_2$ (15 mL) under N$_2$. The mixture was stirred at room temperature overnight until the imine formation was complete (monitored by NMR). The solvent was removed in vacuo, the solid residue dissolved in 50% MeOH/CH$_2$Cl$_2$ (40 mL) and the solution cooled to 0° C. NaBH$_4$ (14.42 mmol) was added in small portions to the solution and the mixture was stirred at rt overnight. The solvent was removed in vacuo, the solid residue dissolved in CH$_2$Cl$_2$ (40 mL) and washed with Na$_2$CO$_3$ solution (10% aq. 3×30 mL). The CH$_2$Cl$_2$ layer was dried over anhydrous Na$_2$SO$_4$, filtered and removed in vacuo to give an oily residue. The oil was purified by flash column chromatography (5% MeOH/CHCl$_3$) to yield the product 12a as a pale-yellow, thick oil (75%). R$_f$=0.3 (5% MeOH/CHCl$_3$); $^1$H NMR (CDCl$_3$) δ 8.20 (m, 3H), 7.85 (d, 2H), 7.43 (m, 2H), 7.36 (m, 2H), 5.32 (t, 1H), 4.52 (s, 2H), 3.10 (q, 2H), 2.77 (t, 2H), 1.56 (q, 2H), 1.39 (s, 9H); $^{13}$C NMR (CDCl$_3$) δ 156.0, 131.3 (2C), 130.1 (2C), 129.0 (2C), 127.0 (2C), 125.9 (2C), 124.8 (2C), 124.0 (2C), 78.7 (2C), 48.5, 45.8, 39.4, 29.9, 28.5. HRMS (FAB) m/z calcd. for C$_{23}$H$_{28}$N$_2$O$_2$ (M+H)$^+$ 365.2224; found 365.2208.

EXAMPLE 12

Synthesis of [3-(Anthracen-9-ylmethyl-ethyl-amino)-propyl]-carbamic acid tert-butyl ester (12b)

Bromoethane (489 mg, 4.48 mmol) was dissolved in anhydrous acetonitrile and was added to the stirring mixture of compound 12a (545 mg, 1.5 mmol) and anhydrous K$_2$CO$_3$ (620 mg, 4.48 mmol). The mixture was then stirred at 75° C. under a N$_2$ atmosphere overnight. After the confirmation of the disappearance of the 12a by TLC, the solution was concentrated under reduced pressure. The residue was dissolved in CH$_2$Cl$_2$ (20 mL) and washed three times with aqueous sodium carbonate. The organic layer was separated, dried with anhydrous Na$_2$SO$_4$, filtered and concentrated under vacuum. Flash column chromatography of the residue gave 12b as a light yellow oil. Yield 80%; R$_f$=0.35 (3% MeOH/CHCl$_3$); $^1$H NMR (CDCl$_3$) δ 8.39 (d, 2H), 8.30 (s, 1H), 7.90 (d, 2H), 7.40 (m, 4H), 4.54 (br t, 1H), 4.37 (s, 2H), 2.74 (q, 2H), 2.60 (q, 2H), 2.39 (t, 2H), 1.44 (q, 2H), 1.31 (m, 9H), 1.12 (t, 3H); $^{13}$C NMR (CDCl$_3$) δ 155.7, 131.3 (2C), 131.2 (2C), 130.4 (2C), 129.0 (2C), 127.5 (2C), 125.7 (2C), 124.8 (2C), 78.3, 50.6, 50.5, 47.7, 39.1, 28.6 (3C), 26.6, 11.8. HRMS (FAB) m/z calcd. for C$_{25}$H$_{32}$N$_2$O$_2$ (M+H)$^+$ 393.2537; found 393.2523.

EXAMPLE 13

Synthesis of N$^1$-Anthracen-9-ylmethyl-N$^1$-ethyl-propane-1,3-diamine, Hydrochloride salt (12c)

A solution of 12b (400 mg, 1.02 mmole) was dissolved in absolute ethanol (13 mL) and stirred at 0° C. for 10 minutes. A 4N HCl solution (22 mL) was added to the reaction mixture dropwise and stirred at 0° C. for 20 minutes and then at room temperature overnight. The solution was concentrated in vacuo to give 12c as a yellow solid in 90% yield. $^1$H NMR (D$_2$O) δ 8.42 (s, 1H), 8.0 (m, 4H), 7.71 (m, 2H), 7.61 (m, 2H), 4.87 (s, 2H), 3.34 (br q, 2H), 3.14 (br t, 2H), 2.81 (t, 2H), 2.00 (q, 2H), 1.40 (t, 3H); $^{13}$C NMR (D$_2$O): δ 133.8, 133.3 (3C), 132.4 (2C), 130.7 (2C), 128.2 (2C), 125.1 (2C), 121.5 (2C), 52.0, 51.9, 39.2 (2C), 24.5, 11.3. HRMS (FAB) calcd for C$_{20}$H$_{24}$N$_2$.2HCl (M+H−2HCl)$^+$ 293.2012, Found 293.2009.

EXAMPLE 14

Synthesis of 3-[(Anthracen-9-ylmethyl)-amino]-propan-1-ol, 14a

To a stirred solution of 3-amino-1-propanol, 15a (0.87 g, 11.65 mmol) in 25% MeOH/CH$_2$Cl$_2$ (20 mL), was added a solution of aldehyde 8 (2.00 g, 9.7 mmol) in 25% MeOH/CH$_2$Cl$_2$ (15 mL) under N$_2$. The mixture was stirred at room temperature overnight until the imine formation was complete (monitored by NMR). The solvent was removed in vacuo, the solid residue dissolved in 50% MeOH/CH$_2$Cl$_2$ (40 mL) and the solution was cooled to 0° C. NaBH$_4$ (29.1 mmol) was added in small portions to the solution and the mixture was stirred at rt overnight. The solvent was removed in vacuo, the solid residue dissolved in CH$_2$Cl$_2$ (40 mL) and washed with 10% aq. Na$_2$CO$_3$ solution (3×30 mL). The CH$_2$Cl$_2$ layer was separated, dried over anhydrous Na$_2$SO$_4$, filtered and removed in vacuo to give an oily residue. The oil was purified by flash column chromatography (6% MeOH/CHCl$_3$) to yield the product 14a as a pale yellow thick oil (78%), R$_f$=0.3 (6% MeOH/CHCl$_3$); $^1$H NMR (CDCl$_3$) δ 8.39 (s, 1H), 8.27 (d, 2H), 7.99 (d, 2H), 7.52 (m, 2H), 7.45 (m, 2H), 4.71 (s, 2H), 3.79 (t, 2H), 3.09 (t, 2H), 1.74 (q, 2H).

EXAMPLE 15

Synthesis of 3-(Anthracen-9-ylmethyl-ethyl-amino)-propan-1-ol, 14b

Bromoethane (616 mg, 5.65 mmol) was dissolved in anhydrous acetonitrile and was added to the stirring mixture of compound 14a (500 mg, 1.9 mmol) and anhydrous K$_2$CO$_3$ (781 mg, 5.7 mmol). The mixture was then stirred overnight at 75° C. under a N$_2$ atmosphere. After confirmation of the disappearance of 14a by TLC, the solution was concentrated under reduced pressure. The residue was dissolved in CH$_2$Cl$_2$ (20 mL) and washed three times with aqueous sodium carbonate. The organic layer was separated, dried with anhydrous Na$_2$SO$_4$, filtered and concentrated under vacuum. Flash column chromatography of the residue gave 14b as a light yellow oil. Yield 82%; R$_f$=0.35 (3% MeOH/CHCl$_3$); $^1$H NMR (CDCl$_3$) δ 8.28 (m, 3H), 7.86 (d, 2H), 7.44 (m, 2H), 7.36 (m, 2H), 4.29 (s, 2H), 3.15 (t, 2H), 2.65 (q, 2H), 2.52 (t, 2H), 1.43 (q, 2H), 1.16 (t, 3H); $^{13}$C NMR (CDCl$_3$) δ 131.2, 131.1, 129.3, 129.0, 127.6, 125.8, 124.8, 124.4, 63.4, 52.6, 50.5, 47.7, 28.1, 11.6. HRMS (FAB) m/z calcd. for C$_{20}$H$_{23}$NO (M+H)$^+$ 294.1852; found 294.1859.

EXAMPLE 16

Synthesis of N1-Anthracen-9-ylmethyl-propane-1,3-diamine, Hydrochloride salt (16)

A solution of 12a (200 mg, 0.51 mmole) was dissolved in absolute ethanol (6 mL) and stirred at 0° C. for 10 minutes. A 4N HCl solution (10 mL) was added to the reaction mixture dropwise and stirred at 0° C. for 20 minutes and then at room temperature overnight. The solution was concentrated in vacuo to give 16 as a yellow solid in 90% yield. $^1$H NMR (CD$_3$OD) δ 8.69 (s, 1H), 8.39 (d, 2H), 8.15 (d, 2H), 7.74 (m, 2H), 7.60 (m, 2H), 5.33 (s, 2H), 3.45 (t, 2H), 3.12 (t, 2H), 2.23 (q, 4H); $^{13}$C NMR (CD$_3$OD): δ 6 132.6, 132.0, 131.6, 130.6, 129.0, 126.7, 124.0, 122.5, 46.6, 44.6, 38.1, 25.4. HRMS (FAB) calcd for C$_{18}$H$_{20}$N$_2$.2HCl (M+H−2HCl)$^+$ 265.1699, Found 265.1704.

EXAMPLE 17

Biological evaluation of polyamine derivatives

In terms of Table 1, L1210 cells are mouse leukemia cells and are the gold standard in terms of evaluating polyamine cytotoxicity data due to a plethora of prior data in this cell line for other polyamine structures. Clearly 7a was similar in all respects to 4a (Table 1). The fact that similar alterations in the structure of 7a and 4a gave the same biological response suggests that they are hitting the same biological target. Low IC$_{50}$ values in Table 1 suggest greater cytotoxicity of the drug. The lower the K$_i$ value, the higher the affinity of the drug for the polyamine transporter (PAT) on the cell surface. Chinese hamster ovary (CHO) cells and a mutant line without an active PAT (CHO-MG) also evaluated the PAT selectivity of these drugs. High (CHO-MG/CHO) IC$_{50}$ ratios suggest a highly selective PAT substrate. Inspection of Table 1 suggests that 7a is an effective mimic of 4a (both have low IC$_{50}$ values), but does not use the PAT for cellular entry (both have low CHO-MG/CHO IC$_{50}$ ratio).

shown in Table 2, all of the derivatives gave medium to high levels of inhibition in the assay, except 4b and 7b. In this regard, most of the new materials provided similar inhibition as 4a.

Note: the disc assay itself is binary. The tested compound is either as good as or worse than 4a. Compounds that are better than 4a will only give the same maximal response (90-100% inhibition). Future work will be necessary to see which of the most active compounds (6a, 6b, 7a, 12c, 13b, 16, 20, 21, and 24) are best in vivo in terms of slowing the spread of cancers (anti-metastatic activity).

Fly Stocks: 20 female and 5 male wild type Oregon variant of *Drosophila melanogaster* interbred in blue food medium for 24 hours then flies are removed. Third instar wall-crawling larvae collected then dissected on the sixth day. Flies kept in 25° C. incubation chamber.

Blue Food Preparation: Standard corn meal medium heated then mixed completely with aqueous 1% Bromophenol Blue. The food medium is cooled for one day or more before use.

Dissection Medium: Ringer's Buffer with 10 uL 0.1% BSA. Ringer's Medium consists of 130 mM NaCl, 5 mM KCl, 1.5 mM CaCl$_2$-2H$_2$O. Stored at room temperature (23° C.), BSA added before dissection.

Cultivation Medium: Minimal Robb's Medium with 10 uL 0.1% BSA. Minimal Robb's Medium consists of 40 mM KCl, 0.4 mM KH$_2$PO$_4$, 40 mM NaCl, 0.4 mM NaH$_2$PO$_4$-7H$_2$O, 1.2 mM MgSO$_4$-7H$_2$O, 1.2 mM MgCl$_2$-6 H$_2$O, 1 mM

TABLE 1

Biological evaluation of polyamine derivatives in L1210, CHO and CHO-MG cells.$^a$

| Compd (tether) | L1210 IC$_{50}$ in μM | L1210 K$_i$ value (μM) | Ref | CHO-MG IC$_{50}$ in μM | CHO IC$_{50}$ in μM | IC$_{50}$ Ratio$^b$ |
|---|---|---|---|---|---|---|
| 4a: dihydroMotu (3,3) | 3.0 (±0.5) | 9.9 (±0.5) | 3 | 10.0 (±2.6) | 10.5 (±1.6) | 1 |
| 4b: dihydroMotu (4,4) | 18.5 (±2.9) | 6.2 (±0.5) | 3 | 28.2 (±5.6) | 30.0 (±4.1) | 1 |
| 6a: Ant-methyl (3,3) | 1.8 (±0.4) | 33.4 (±2.6) | 3 | 3.4 (±0.5) | 1.9 (±0.4) | 1.8 |
| 6b: Ant-methyl (4,4) | 0.30 (±0.04) | 1.8 (±0.1) | 3 | 66.7 (±4.1) | 0.45 (±0.10) | 148 |
| 6c: Ant-ethyl (4,4) | 3.5 (±0.7) | 1.6 (±0.1) | 8 | 33.5 (±7.1) | 9.8 (±1.1) | 3.4 |
| 6d: Ant-propyl (4,4) | 76.3 (±4.8) | 1.1 (±0.1) | 8 | 130.8 (±5.5) | 130.1 (±7.1) | 1 |
| 7a: N$^1$-ethyl-N$^1$-Ant-methyl (3,3) | 2.2 (±0.1) | 23.5 (±0.9) |  | 4.0 (±0.3) | 5.3 (±0.4) | 0.8 |
| 7b: N$^1$-ethyl-N$^1$-Ant-methyl (4,4) | 22.2 (±1.2) | 24.4 (±1.5) | 3 | 21.9 (±0.9) | 22.2 (±0.7) | 1 |

$^a$Definitions used in Table 1, column 1: Ant = anthracen-9-yl, dihydroMotu = dihydromotuporamine; column 4: Ref denotes the reference number in which the data was originally reported. A blank in the Ref column denotes new data. Cells were incubated for 48 h with the respective conjugate.
$^b$The IC$_{50}$ ratio denotes the (CHO-MG/CHO) IC$_{50}$ ratio, a measure of PAT selectivity.

EXAMPLE 18

Inhibition of Motuporamine Mimic Agents

DihydroMotuporamine C, 4a, was used to develop an imaginal disc assay in *Drosophila* flies. The imaginal leg discs were collected by microscopic dissection from maggots. The assay reproducibly showed that (at 18 μM) 4a gave very high inhibition (≧87%) of development of the imaginal disc (Table 2). Inhibition was measured as failure of the disc to fully develop into a fly leg after 15 hr of incubation in Robb's growth medium. This presumably occurs by overactivation of Rho, an important signaling pathway in development. Hyper-stimulation of this pathway is sufficient to block development of the fly leg.

Using this concentration (18 μM) the panel of mimics were assayed (4, 6a, 6b, 7a, 7b, 12c, 13b, 16, 20, 21, and 24). As CaCl$_2$-2 H$_2$O, 10 mM Glucose, 0.2 mM L-asparagine, 4.0 mM L-glutamine, 0.16 mM Glycine, 0.64 mM L-leucine, 0.32 mM L-proline, 0.16 mM R-Serine, 0.64 mM L-valine. Stored at −25° C. One day before dissection, aliquot defrosted in 4° C. Add BSA then warmed to room temperature (23° C.) before dissection.

0.1% BSA: 0.1 g BSA fraction V (Sigma#A-9647) in 10 mL distilled H$_2$O. Stored at 4° C.

Developmental Hormone: 1 mg 20-hydroxyecdysone (Sigma #H-5142) in 1 mL 100% Ethanol. Stored at −25° C. Before use, stock is diluted 10× (1 mL added to 9 mL of 100% Ethanol). 10 μL of diluted 20-hydroxyecdysone is added to culture.

Dissection Procedures: Third instar larvae are removed from cultivation bottle with a wetted brush and washed in dH$_2$O to remove food medium clinging to larvae. The cleaned larvae are dissected in Ringer's Medium using forceps. The imaginal discs are washed in fresh Ringer's Medium, and then cultivated with 1 mL of Robb's Medium in 12-well culture plate. Each culture well should have 30~40 imaginal discs.

Culturing Procedures: In a larger container, place the 12-well culture plate on a moist towel, then seal the large container. Cultivate at 25° C. for 15 hours. Evaluation: Three categories will be used to grade the eversion of each imaginal disc. Full Eversion—the leg is fully extended from the disc. Partial Eversion—the leg is protruding from the epithelial. No Eversion—no sign of any protrusion.

TABLE 2

Eversion Inhibition by new compounds at 18 μM in an Imaginal Disc Assay[a]

| Compound | % Inhibition |
|---|---|
| 4a (Motu 3,3) | 87 |
| 4b (Motu 4,4) | 0 |
| 6a (Ant 3,3) | 60 |
| 6b (Ant 4,4) | 97 |
| 7a (AntNEt 3,3) | 95 |
| 7b (AntNEt 4,4) | 8 |
| 12c (AntNEtDiamine 3) | 79 |
| 13b (Ant Diamine 4) | 91 |
| 16 (Ant Diamine 3) | 92 |
| 20 (Ant NEt aminoalcohol 3,3) | 38 |
| 21 (AntNEt aminoether 3,3) | 36 |
| 24 (AntNEt acetamide 3,3) | 58 |

[a]The error is typically near 10-15% for this type of developmental measurement.

While various embodiments of the present invention have been shown and described herein, it will be obvious that such embodiments are provided by way of example only. Numerous variations, changes and substitutions may be made without departing from the invention herein. Accordingly, it is intended that the invention be limited only by the spirit and scope of the appended claims. The teachings of all references cited herein are incorporated in their entirety to the extent not inconsistent with the teachings herein.

What is claimed is:

1. A pharmaceutical composition cytotoxic to cancer cells wherein said composition comprises one or more compounds of Formula I, or a pharmaceutically acceptable salt thereof, and a pharmaceutically acceptable carrier, wherein Formula I is:

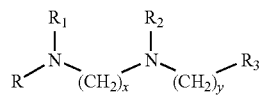

Formula I wherein R is anthracen-9-ylmethyl;
$R_1$ is ethyl;
$R_2$ is hydrogen, or BOC;
$R_3$ is $NH_2$ or NHBOC; and
x=1-16 and y=1-16.

2. The composition of claim 1, wherein said composition comprises one or more compounds of Formula I wherein:
R=anthracen-9-ylmethyl, $R_1$=ethyl, $R_2$=H, $R_3$=NH2, x=3, and y=3;
R=anthracen-9-ylmethyl, $R_1$=ethyl, $R_2$=H, $R_3$=NH2, x=4, and y=4;
R=anthracen-9-ylmethyl, $R_1$=ethyl, $R_2$=BOC, $R_3$=NHBOC, x=3, and y=3; or
R=anthracen-9-ylmethyl, $R_1$=ethyl, $R_2$=BOC, $R_3$=NHBOC, x=4, and y=4.

3. A method of killing cancer cells in a patient in need thereof comprising administering one or more compounds according to Formula I or II, or a pharmaceutically acceptable salt thereof, effective to kill cancer cells in said patient, wherein Formula I is:

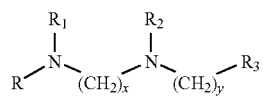

Formula I wherein R is anthracen-9-ylmethyl;
$R_1$ is ethyl;
$R_2$ is hydrogen or BOC;
$R_3$ is $NH_2$ or NHBOC; and
x=1-16 and y=1-16.

* * * * *